US007182935B2

(12) United States Patent
Ribeiro de Nazaré et al.

(10) Patent No.: US 7,182,935 B2
(45) Date of Patent: Feb. 27, 2007

(54) BACTERIAL PLAQUE EVIDENCING COMPOSITION BASED ON NATURAL COLORANTS

(75) Inventors: Raimunda Fatima Ribeiro de Nazaré, Belem do Para (BR); Danielle Tupinamba Emmi, Belem do Para (BR); Regina Fatima Feio Barroso, Belem do Para (BR); Patricia Oliveira da Rocha, Belem do Para (BR)

(73) Assignees: Empresa Brasileira De Pesquisa Agropecuaria Embrapa (BR); Universidade Federal Do Para (BR)

( * ) Notice: Subject to any disclaimer, the term of this patent is extended or adjusted under 35 U.S.C. 154(b) by 362 days.

(21) Appl. No.: 10/173,844

(22) Filed: Jun. 19, 2002

(65) Prior Publication Data
US 2004/0002132 A1  Jan. 1, 2004

(51) Int. Cl.
*A61B 5/00* (2006.01)
*A61K 36/00* (2006.01)
(52) U.S. Cl. .................. 424/9.71; 424/725; 424/777; 435/34
(58) Field of Classification Search ............. 424/725, 424/777, 9.71; 435/34
See application file for complete search history.

(56) References Cited

U.S. PATENT DOCUMENTS

| 3,309,274 | A |   | 3/1967  | Brilliant |
|---|---|---|---|---|
| 3,624,219 | A |   | 11/1971 | Perlitsh |
| 3,997,658 | A |   | 12/1976 | Block et al. |
| 4,302,439 | A |   | 11/1981 | Selwyn |
| 4,431,628 | A |   | 2/1984  | Gaffar |
| 4,459,277 | A |   | 7/1984  | Kosti |
| 4,517,172 | A |   | 5/1985  | Southard |
| 4,590,061 | A | * | 5/1986  | Southard ............ 424/9.71 |
| 4,666,700 | A | * | 5/1987  | Frysh ............... 424/9.71 |
| 4,992,256 | A | * | 2/1991  | Skaggs et al. ........ 424/9.71 |
| 5,190,743 | A | * | 3/1993  | Simone et al. ........ 424/9.71 |
| 5,458,892 | A | * | 10/1995 | Yatka et al. ............ 426/5 |

OTHER PUBLICATIONS http://216.239.41.104/search?q=cache:gA8-qeJ6ehlJ:www.acaiforlife.com/faqs/acai_faq.cfm+ACAI+AND+COLORING+AND+EXTRACT&hi=en [Life Dynamics] "Other facts about Acai" one page abstracted.*
Cabrita et al "Food Chemistry" 68 (2000) p. 101-107.*
Nazare et al, "Study to Identify Dye-Producing Plants in Amazonian Flora"1996, CPATU pp. 173-191 Translated Copy of Reference 15.*
P. Axelsson et al., "The effect of a preventive program on dental plaque, gingivites and caries in schoolchildren." Journal of Clinical Periodontology. (1974) vol. 1, p. 126-138.
S.S. Arnim, "The use of disclosing agents for measuring tooth cleanliness." Journal of Periodontology. (1963) vol. 34, p. 227-245.

A. Baliane, "Cultura do urucueiro," *Empresa de Assisténcia Técnica e Extensáo Rural do Estedo do Rio de Janeiro*, Niteról, (1984) p. 5-16.
Y.P. Buischi et al., "Controle Mecánico da Placa Dental Realizado pelo Paciente," In: *PromoçÁo da Saude Bucal*, $2^{nd}$ Ed., L. Kriger, Ed. (1999) Chapter 6, p. 113-127, Artes Médicas, Sá o Paulo.
R.R.B. Camarez et al., Estabilidades das antocianinas do calice Hibiscus sabdariffa L. In: Resumos IV Congresso Brasileiro de Corantes Naturais. Joáo Pessoa—PB. 21-23/05/2000. TTC—4. p. 40.
P.R.N. Carvalho, "Extraçáo e Utilizaçáo do Corante de Urucum," In: *A Cultura do Urucum no Brasil*, Vitória da Conquista, BA, UESB., (1990) Chapter 12, p. 69-76.
P. Collins, "The role of annatto in food colouring." Food Ingredients & Processing International, (1992) p. 23-27, Rickamansworth, Hertfordshire, UK: Turret Group ptc.
J.L. Couto et al., "Prevençáo e MotivaçÁo na Clinica Odontológica," In: *Promoçáo da Saude Bucal*, $2^{nd}$ Ed., L., Kriger, Ed. (1999) Chapter 6, p. 59-80, Artes Médicas, Sáo Pautol.
C. Dawes et al., "The Nomenclature of the integuments of the enamel surface of the teeth." Brit. Dent. J. (1973) vol. 15, p. 65-68.
T. Fuleki et al., "Quantitative methods for anthocyanins. 2-Determination of total anthocyanin and Degradation Index for Cranberry Juice," J. Food Sci. (1968) vol. 33, p. 78-83.
I.S.S. Guimaráes, "Corantes naturais: os sucedáneos dos artificiais," *Revista Brasileira de Corantes Naturais* (1996) vol. 2 No. 1, p. 98-110.
P.F. Kramer et al., "Tratamento Náo Invasivo," In: *Promoçáo de Saúde Bucal em Odontopediatria*, (1997) Chapter 6, p. 89-112, Artes Médicas, Sáo Paulo.
E.M. Kuskoski et al., Estudo comparativo da estabilidade das antocianinas do Baguacu, Jambaláo da Uva. In: *Resumos IV Congresso Brasileiro de Corantes Naturais*, Joáo Pressoa—PB. 21-May 23, 2000. TTC—5. p. 41.

(Continued)

*Primary Examiner*—Herbert J. Lilling
(74) *Attorney, Agent, or Firm*—Finnegan, Henderson, Farabow, Garrett & Dunner LLP (57) ABSTRACT

The present invention deals with a composition for evidencing bacterial plaque based on natural colorants comprising at least one concentrated solution of natural colorant selected from the group consisting of colorants extracted from the acai (*Euterpe oleracea*) and colorants extracted from urucum (*Bixa orellana*), in a pharmaceutically acceptable vehicle and, optionally, acceptable pharmaceutical additives. Preferentially, in the case of the acai solution, the concentration varies from 60 to 95% of concentrated extract, whilst for the urucum solution, the concentration varies between 56 and 90% of concentrated extract.

Also preferentially, in solutions containing a mixture of the extracts, these will be present in a proportion that varies from 10:1 to 1:1.

9 Claims, 3 Drawing Sheets

OTHER PUBLICATIONS

E.M. Kuskoski et al., Identificação de antocianinas nos frutos de Baguaçu (*Eugenia umbeliflora* BERG). In: Resumos IV Congresso Brasileiro de Corantes Naturais. Joáo Pessoa—PB. 21-May 23, 2000. TTC—6. p. 42.

N.T. Lascala et al., "Higienização Bucal—Fisioterapia—Aspectos Preventivos em Odontologia," In: *Prevençáo na Clinica Odontolgica—Promoçáo de Saúde Bucal*, N.T. LASCALA, ED., (1997) Chapter 9, p. 119-145, Artes Médicas, Sáo Paulo.

H. Loe et al., "Peridontal Disease in Pregnancy." J. Periodontal Disease in Pregnancy. (1963) vol. 21, p. 533-551.

M. Maltz et al., "Diagnóstico da Doença Cárie," In: *Promoçáo da Saúde Bucal*, 2nd Ed., L. Kriger, Ed. (1999) Chapter 4, p. 71-91, Artes Médicas, Sáo Paulo.

P.T. Marques et al., Comportamento do extrato do jamboláo a diferentes pHs. In: Resumos IV Congresso Brasileior de Corantes Naturais. Joáo Pessoa—PB. 21-May 23, 2000. TTC—7. p. 43.

R.F.R. de Nazare et al., "Análise quantativa dos teores de corantes em frutos de açaizeiro," Boletim de Presquisa, (1998) No. 210, p. 5-18.

R.F.R. de Nazare et al., "Estudo para a identificaçáo de Vegetais Produtores de Corantes Ocorrentes na Flora Amazónica," EMBRAPA. Centro Agroflorestal da Amazónia Oriental (Belém, PA). Geraçáo de Tecnologia Agroindustrial para o desenvolvimento do tropical umido. Belém: EMBRAPA—CPATU / JICA, (1996) p. 173-191 (EMBRAPA—CPATU. Documentos, 85).

R.F.R. de Nazare et al., "Potencialidade de Plantas Amazónicas Productoras de Corantes Naturals," *Revista Brasileira de Corantes Naturais* (1996) vol. 2, No. 1, p. 166-168.

C.R.M.D. Rodrigues et al., "Aspectos Preventivos em Odontopediatria," In: *Prevençáo na Clinica Odontológia—Promoçáo de Saúde Bucal*, N.T. Lascala, Ed. (1997) Chapter 7, p. 83-102, Artes Médicas, Sáo Paulo.

K. Zimber, "Corantes de Urucum—Aplicaçáo em Alimentos Diversos," In: II Seminário de Corantes Naturais para Alimentos, I Simpósio International do Urucum Campinas, SP., (1991) p. 265-267.

Lichtenthäler, R., "Optimisation of the Total Oxidant Scavenging Capacity Assay and Application on *Euterpe oleracea* Mart. (Açal) Pulps and Seeds,", (2004) Inaugural-Dissertation zur Erlangung der Doktorwürde der Mathematisch-Naturwissenschaftlichen, Fakultät der Rheinischen Friedrich-Wilhelms—Universität zu Bonn, Bonn, Germany.

Iaderoza M. et al., Anthocyanins from Fruit of Açai (*Euterpe oleracea* Mart.) and Jucara (*Euterpe edulis* Mart.) (1992) Trop. Sci. vol. 32, pp. 41-46.

Navarro M., et al., "Usefulness of saliva for measurement of 3,4-methylenedioxymethamphetamine and its metabolites: correlation with plasma drug concentrations and effect of salivary pH." Clin Chem. Oct. 2001;47(10): 1788-95.

\* cited by examiner

BACTERIAL PLAQUE EVIDENCING COMPOSITION BASED ON NATURAL COLORANTS

FIELD OF THE INVENTION

The present invention refers to compositions based on natural colorants extracted from açai (*Euterpe oleracea*) and urucum (*Bixa orellana*) used to evidence bacterial plaque.

BACKGROUND OF THE INVENTION

In the past, the main concern in odontology was to diagnose and treat established lesions derived from caries. There was no known means of controlling the disease and the only treatment possible was the removal of the caried tissue to impede the progress of the lesion, restoring that dental element. Today, with the increase of knowledge, this concept has changed and odontology has turned to promoting health through an early diagnostic followed by counseling to enable the patient to control the disease himself. In this manner, epidemiological studies have shown that there has been a reduction of caries and gingival disease percentages.

Bacterial plaque is considered one of the aetiological factors of dental caries and periodontal disease which places therefore great importance on the application of preventive measures as a means of keeping buccal structures healthy.

Dental plaque is a well-organised structure that forms over the surface of teeth, restoration and protheses and consists, mainly, of an organic matrix derived from saliva and from bacteria existing in the buccal cavity.

The mechanism for forming plaque occurs with bacteria of the most diverse forms present in saliva (coccus, bacillus, coccobacillus, etc.) that begin depositing until totally covering the dental surface. The thickness of the bacterial plaque is related to the ingestion of saccharose and with buccal hygiene, and becomes a factor that causes demineralisation of the enamel that results in dental caries and periodontal irritation leading to infectious periodontal processes. The effective removal of these deposits becomes essential for the control of diseases associated to plaque.

To this end, various recourses must be used to motivate the patient to practice buccal hygiene. Experience has shown that the majority of patients are not sufficiently motivated to practice good buccal hygiene merely by being informed that plaque means that a bacteria colony is growing around their teeth and that this plaque causes caries and diseases of the gums, therefore requiring frequent removal. However, the global concept of what plaque means and what it is capable of doing to tissues may become more striking to the patient through visualisation, in the sense that each patient will be able to observe the plaque in situ.

The resources used presently to motivate patients range from direct instruction (posters, graphs and macro-models) (Dotto, C. A. and Sendik, W. R. Atlas de higienizacao bucal. Sao Paulo: Panamed, 88p., 1982. In: LASCALLA, N. T. Prevenção na Clínica Odontológica. Prevenção e motivação na Clínica Odontológica. P 59–80) to indirect instruction or self-instruction (explanatory pamphlets, films, information about diet, plaque and buccal hygiene) (COUTO, J. L., COUTO, R. S. Programa de motivação do paciente. RGO (Porto Alegre), v. 40, n. 6. P. 433–438, November/December, 1992).

Self-care through buccal hygiene (brushing and use of dental floss) is efficient in the control of bacterial plaque, however it is necessary to motivate the patient to perform the appropriate hygiene capable of promoting efficient mechanical disruption to avoid buccal diseases.

Thus, the use of compositions for evidencing plaque has been recommended by professionals with the intent of increasing the detection and the effective removal of plaque. These disclosing solutions contain colouring agents or pigments that are absorbed by the plaque and render it visible so as to be eliminated. The majority of the disclosing compositions are based on iodine or organic colorants.

Organic colorants have been almost universally employed for use in disclosing compositions due to their high degree of efficiency. However, in the majority of cases these colorants possess very unpleasant flavours that are not effectively masked by any of the known flavoring agents or sweeteners.

Organic disclosing agents such as, amongst others, erythrosin (FDC Red #3) are described in patents U.S. Pat. No. 3,309,274, U.S. Pat. No. 3,624,219, U.S. Pat. No. 3,997,658, U.S. Pat. No. 4,302,439, U.S. Pat. No. 4,992,256 and U.S. Pat. No. 4,459,277. The patent U.S. Pat. No. 3,624,219 mentions that erythrosin is the agent of preference compared to others such as Amaranth and Brilliant Blue, as these latter are excessively soluble in water and do not penetrate or persist in the mouth in the proportions desired for the purposes of disclosing plaque. The patent U.S. Pat. No. 3,309,274 uses the synthetic fluorescent colorants FDC Colors Red #3, Green #8, Red #19, Red #22, Red #28, Yellow #7 and Yellow #8 which are invisible to the human eye in normal daylight or artificial light and only become visible through the use of light on the appropriate wavelength.

Erythrosin was recommended as a colorant rather than fuchsin, a solution of thymerosal (Merthiolate®) and neutral red for use in teaching buccal hygiene and in the prevention of dental diseases. The solution of thymerosal is considered a weak disclosing agent, with an unpleasant taste that takes time to leave the mouth, as well as containing a substance that is considered cancerous. Fuchsin is also suspected of being cancerous. (ARNIM, S. S.; "The use of disclosing agents for measuring tooth cleanliness". Journal of Periodontology. 34, 227–245. 1963).

However, erythrosin also presents disadvantages inasmuch as it possesses a very high retention time with an undesirable colouring of the patient's mouth, a weak contrast between the gingival tissue and the coloured plaque as well as an unpleasant taste.

In this sense, natural colorants have been suggested as alternatives to the use of synthetic organic colorants for use in the practice of buccal hygiene motivation. According to Guimaraes (GUIMARÃES, I. S. S., Corantes naturais: os sucedâneos dos artificiais. In: Revista Brasileira de Corantes Naturais. Sociedade Brasileira de Corantes Naturais. Embrapa—CPATU, vol 2, n.1, p.98–110, 1996), artificial colorants have disadvantages which natural colorants do not present. Some artificial colorants provoke diseases of the thyroid, lesions of the liver, hyperacidity and allergies such as, for example, asthma, rhinitis and rashes.

Examples of natural colorants used to disclose bacterial plaque may be encountered in patents U.S. Pat. No. 4,431,628 and U.S. Pat. No. 4,517,172. The patent U.S. Pat. No. 4,431,628 refers to a method for indicating the presence of bacterial plaque, comprising an efficient quantity of natural colorant extracted from sugar beet. This method employs a disclosing composition that may be provided in the form of tablets, solutions, gels or aerosols. The roots of the sugar beet contain red and yellow pigments that belong to the betalayin class—quaternary ammonia amino acids—which are divided into betacyanins (red) and betaxanthins (yellow).

Patent U.S. Pat. No. 4,517,172 describes a method for the visualisation of plaque, in such a manner that the plaque is visible to the naked eye under ultraviolet light. The method employs a salt of sanguinarine precipitated from extracts of plants selected from the group consisting of *Sanguinaria canadensis, Macleaya cordata, Corydalis sevctvozii, C. ledebouni, Chelidonium majus* and mixtures of these. It presents the inconvenience of requiring ultraviolet light to enable visualisation, which makes frequent use by patients in their homes difficult.

The comments above demonstrate the importance of developing formulations containing plaque evidencing agents of natural origin both efficient and of selective efficiency.

SUMMARY OF THE INVENTION

The objective of the present invention is a new bacterial plaque evidencing composition based on natural colorants.

The present invention is embodied in the form of a composition for evidencing bacterial plaque based on natural colorants comprising at least one concentrated solution of natural colorant selected from the group consisting of colorants extracted from the açai (*Euterpe oleracea*) and colorants extracted from urucum (*Bixa orellana*), in a pharmaceutically acceptable vehicle and, optionally, acceptable pharmaceutical additives.

Preferentially, in the case of the açai (*Euterpe oleracea*) solution, the concentration varies from 60 to 95% of concentrated extract, whilst for the urucum (*Bixa orellana*) solution, the concentration varies between 58 to 90% of concentrated extract.

Also preferentially, in solutions containing a mixture of the extracts, these will be present in a proportion that varies from 10:1 to 1:1.

BRIEF DESCRIPTION OF THE DIAGRAMS

DETAILED DESCRIPTION OF THE INVENTION

In order to facilitate comprehension of the invention some definitions of the essential characteristics of the composition are provided below:

Concentrated solution of colorants extracted from açai (*Euterpe oleracea*): means a solution obtained by the processing of the açai fruit, including at least one stage of extraction by maceration in the preferential proportion of one part of açai fruit for approximately one and a half parts of extractor solvent followed by filtration and recuperation of the liquid phase until obtaining 1000 ml of extract and, finally, concentration to a volume between approximately 4 and 6% of the initial volume (1000 ml).

Concentrated solution of colorants extracted from urucum (*Bixa orellana*): means a solution obtained by the processing of the urucum fruit, including at least one stage of extraction by maceration in the preferential proportion of one part of urucum fruit for approximately two parts of extractor solvent followed by filtration and recuperation of the liquid phase until obtaining 1000 ml of extract and, finally, concentration to a volume between approximately 4 and 6% of the initial volume (1000 ml).

Pharmaceutically acceptable: means the component(s) appropriate for human use, thus, within the acceptable toxicological limits established by an agency qualified for registering drugs, cosmetics and correlates, with the aim of future commercialisation.

For many years the only treatment used in Odontology was curative-reparative therapy. However, the treatment that aims merely to eliminate the symptoms of dental disease does not diminish the necessity of treatment, neither the incidence of teeth loss (FRANDSEN, A. Introduction In: Preventive Dentistry in Practice. Copenhagen, p. 9–14. 1976).

Correa (CORREA, A. P. Análise comparativa dos Efeitos de um Programa Incremental sobre Saúde Oral de seus Beneficiados. Dissertação de Mestrado. Universidade Federal do Rio Grande do Sul. 53p. 1985 In: KRIGER, L. Promoção de Saúde Bucal. Diagnóstico da Doença Cárie. P. 69–91), conducting research about the prevalence of caries in school children concluded that the application of restorative treatment does not promote an effective improvement of buccal health.

For Buischi & Axelsson (BUISCHI, Y. P. and AXELSSON, P. Controle Mecânico da Placa Dental Realizado pelo Paciente. IN: Promoção da Saúde Bucal, ABOPREV. 2 ed. São Paulo: Ed. Artes Médicas, cap. 6, P.113–127. 1999), for the past decades inadequate knowledge about the aetiology and pathogenesis of the carie has made its treatment synonymous to teeth with cavities, but there is a distinction between prevention and treatment of the carie disease. This marked distinction originates in the old end equivocated concept that a tooth develops a cavity directly from a healthy state from one day to another without the occurrence of any intermediate stage. However, during the last decade research has shown that the development of carie disease symptoms involve alterations of the dental enamel, that go from the microscopic dissolution of the individual crystals to the clinically detected lesion.

For Kramer, Feldens and Romano (KRAMER, P. F., FELDENS, C. A. and ROMANO, A. R. Promoção de Saúde Bucal em Odontopediatria. São Paulo: Ed. Artes Médicas, 1997, p. 89–128), the counseling and motivation for plaque control should involve special attention during the eruption periods of the different teeth groups.

According to Couto, Couto and Duarte (COUTO, J. L., COUTO, R. S. and DUARTE, C. A. Prevenção e Motivação na Clínica Odontológica. In: Promoção de Saúde Bucal. São Paulo: Ed. Artes Médicas, cap. 6, p. 59–80), the diffusion of information and instruction as to hygiene techniques will not result, alone, in the practice of effective buccal hygiene on the part of the patient. Only after acquiring personal motivation, or the requirement of maintaining a clean mouth, will the patient obtain satisfactory results.

Promoting self-care is one of the most important strategies in primary health care. This process has the fundamental purpose of making the patient responsible for his own health, teaching him to carry out his part to promote his personal health such as, for example, the daily control of plaque. In this context, the most important role of the dentist is to educate towards better health (BUISCHI & AXELSSON, 1999).

The lack of buccal hygiene is responsible for the onset of the majority of gingivoperiodontal diseases where the control of plaque is fundamental for the prevention of these diseases. (LASCALA, N. T. and MOUSSALLI, N. H. Higienização Bucal—Fisioterapia: Aspectos Preventivos em Odontologia. In: Prevenção na Clínica Odontológica—Promoção de Saúde Bucal. São Paulo: Ed. Artes Médicas, cap. 9, p. 119–143, 1997).

Dawes, Jenkins and Tonge (DAWES, C., JENKINS, G. N. and TONGE, C. H. The Nomenclature of the integuments of the enamel surface of the teeth. Brit Dent J. 115:65–68. 1973), relate that bacterial plaque is a physically stable substance over the tooth, being impossible to remove through rinsing the mouth with water, powerful jets of air or through chewing hard or fibrous foods.

The best method for plaque control is mechanical, which may employ dental floss or ribbon, stimulators, toothpicks and toothpaste, but the most powerful tools are without doubt the toothbrush, the interproximal and dental floss (LASCALA, N. T. and MOUSSALLI, N. H. Higienização Bucal—In: Periodontia Clínica II: especialidades afins. São Paulo: Ed. Artes Médicas, 1989. p. 454–482 1997).

According to Axelsson (AXELSSON, P. A. A Odontologia Preventiva deve basear-se no Controle da Placa Dentária. Sao Paulo: Faculdade de Odontologia da Universidade de São Paulo. Associação Brasileira de Odontologia Preventiva. 63p. 1981 In: LASCALLA, N. T. Prevenção na Clínica Odontológica. Aspectos Preventivos em Odontopediatria. P.81–102), dental cleanliness in reaction to the requirements observed through the use of plaque evidencing is possibly the most efficient manner to remove bacterial plaque, as well as acting as a motivating factor.

For Lascalla & Moussalli (1997), the proven merit of plaque evidencing makes the use of these substances increasingly widespread, being used not just by professionals whilst teaching and giving advice on brushing techniques but also by patients at home, where the areas of plaque revealed can be noted and removed.

An evidencing agent should conform to certain criteria so as to be useful as a means of disclosing plaque. Firstly, the colorant shall be capable of adequately penetrating the deposits and colouring these deposits in a manner as to render these visible to the patient without, however, producing a colouring effect that prolongs overly. This colouring efficiency must be selective so as to identify the areas of plaque formation on all the tooth surfaces and not colour the gingival tissue or other oral tissues. The selective efficiency of the colorant should be associated to the easy removal of the latter from the patient's mouth with simple rinsing or washing after use. Furthermore, the flavour and the colouring should be pleasant and acceptable to the user. Finally, the agent should be innocuous and non-cancerous.

In this sense, the present invention presents new plaque evidencing formulations based on natural colorants extracted from açai and urucum.

The açai fruit (*Euterpe oleracea*) produces colorants of the anthocyanin type that belong to the group of hydrosoluble pigments that present a red colouring in acid pH and green in alkaline pH, together with slow degradation under the effect of the incidence of light. Through analysis of the açai extracts using HPLC (high performance liquid chromatography) the two compounds responsible for pigmenting the açai were detected.

These are anthocyanins with RFs (sample readings) of 0.34 and 0.57 that indicate they are two pigments of the same category—anthocyanins—but with resolution characteristics at two different points (see NAZARE, R. F. R. de, ALVES, S. de MELLO, BARBOSA, W. C., RODRIGUES, I. A., FARIA, J. G. and KUSAHARA, K. Estudo para a identificação de Vegetais Produtores de Corantes Ocorrentes na Flora Amazônica. In: EMBRAPA. Centro Agroflorestal da Amazônia Oriental (Belém, PA). Geração de Tecnologia Agroindustrial para o desenvolvimento do tropical úmido. Belém: EMBRAPA—CPATU/JICA, 1996. p. 173–191 (EMBRAPA—CPATU. Documentos, 85). Because they are hydrosoluble colorants it is necessary to use a fixing agent such as ethylic alcohol in order to obtain better extraction of the pigments. This demonstrates that the colorants present in the concentrated solution obtained from the fruit of the açai are predominantly colorants belonging to the anthocyanin class.

The açai fruit present a better yield and quality of colorant in the period between the months of August and November (NAZARE, R. F. R. de and RIBEIRO, G. de J. F. Análise quantativa dos teores de corantes em frutos de açaizeiro. Belém: Embrapa—CPATU. Boletim de Pesquisa, 210).

The extraction of the colorant is done through processes with solvents known to those skilled in the art and does not employ other than routine methodology and conditions. Examples of this process may be encountered in various publications available (see FULEKI, T. and FRANCIS, F. J. Quantitative methods for anthocyanins. 1—Extraction and determtination of total anthocyanin in cranberries. J. Food Sci. 33. 1968. P. 78–83.; NAZARE, 1996; NAZARE, 1998; CAMAREZ, R. R. B.; KUSKOSKI, E. M.; BRIGHENTE, I. M. and FETT, R. Estabilidade das antocianinas do calice Hibiscus sabdariffa L. In: Resumos IV Congresso Brasileiro de Corantes Naturais. João Pessoa—PB. 21–23, May 2000. TTC—4. P. 40.; KUSKOSKI, E. M.; MARQUES, P. T. and FETT, R. Estudo comparativo da estabilidade das antocianinas do Baguacu, Jambolão e da Uva. In: Resumos IV Congresso Brasileiro de Corantes Naturais. João Pessoa—PB. 21–23, May 2000. TTC—5. P. 41.; KUSKOSKI, E. M.; RUZZA, A. A.; PAIVA, E.; BRIGHENTE, I. M. C. and FETT, R. Identificação de antocianinas nos frutos de Baguaçu (Eugenia umbliflora BERG). In: Resumos IV Congresso Brasileiro de Corantes Naturais. João Pessoa—PB. 21–23, May 2000. TTC—6. P. 42.; MARQUES, P. T. and FETT, R. Comportamento do extrato do jambolão a diferentes pHs. In: Resumos IV Congresso Brasileiro de Corantes Naturais. João Pessoa—PB. 21–23, May 2000. TTC—7. P. 43.).

In a preferred embodiment of the invention, the extraction is done by the addition of an alcoholic solution to the ripe açai fruit. Afterwards, this material is cold macerated during an appropriate time, in the absence of light, stirred slowly and filtered in a manner as to obtain the first coloured extract. The operation is repeated with extraction by maceration with alcoholic solvent following the same procedure as above, stirring slowly and filtering in a manner as to obtain a second coloured extract. Both extracts are concentrated together in a rotary evaporator.

As for the colorants of urucum (*Bixa orellana*), according to Zimber (ZIMBER, K. Corantes de Urucum—Aplicação em Alimentos Diversos. In: II Seminário de Corantes Naturais para Alimentos_I Simpósio International do Urucum_Resumos. Campinas, SP. p. 265–267. 1991), there are in its seeds a group of carotenoids containing mainly bixin and norbixin. Bixin possesses a yellow-orange colour and can be extracted directly with vegetable oils, organic solvents or by mechanical processes known to those skilled in the art and does not employ other than routine procedures. Norbixin varies in colour from yellow to reddish orange. However, the colour of the aqueous solutions of this colorant varies with pH and the solubility diminishes with diminishing pH.

According to Carvalho (CARVALHO, P. R. N. Extração e Utilização do Corante de Urucum. In: A Cultura do Urucum no Brasil. Vitória da Conquista, BA, UESB. P. 69–76. 1990), bixin presents liposoluble properties and can be extracted with organic solvents or by mechanical processes through the friction of the seeds and does not employ methods other than routine procedures and conditions known to those skilled in the art. Examples of these processes may easily be found in the literature (see COLLINS, P. The of annatto in food colouring. Food Ingredients & Processing International, Rickamansworth, Hertfordshire, UK: Turret Group plc. 1992. p. 23–27; NAZARE, 1996; BALIANE, A. Cultura do urucueiro. Empresa de Assistência Técnica e Extensão Rural do Estado do Rio de Janeiro. Niterói, 10 p., 1982).

Other artisanal preparations that constitute part of the typical flavour found in the cooking of northern Brazil can be made by using heated vegetable oil and water (CUNHA, L. G. C.; FREIRE, J. M. and FARIAS, E. Diagnóstico da cultura do urucu (*Bixa orellana*) na Ibiapaba—Fortaleza, EPACE, 1978, 37 p.; Batista, F. A. S. & Barbosa, M. M. Utilização de mudas selecionadas: uma alternativa para a melhoria da produtividade de cultura do urucueiro. João Pessoa, EMEPA—PB, 1986. 4 p. EMEPA—PB. Comunicado Técnico, 27; citados por GUIMARÃES, 1996).

Preferentially, the extraction of the urucum colorant is generally done using three methodologies aiming to extract the pigment from the seeds. The first is obtaining the pigment by the abrasion of seeds immersed in vegetable oil heated to 70° C. Another method is the extraction with an alkaline solution, usually sodium or potassium hydroxide, also by the maceration of the seeds in the extractor solution. The third method is the extraction by organic solvents, such as for example acetone or methanol, obtaining extracts with higher pigment levels. The use of this method requires the removal of the solvent and the dissolution of the resulting pigment powder in refined vegetable oil (COLLINS, 1992).

Thus, a hydro-alcoholic solution (5% alcohol) is added to the urucum seeds. Afterwards, this material is cold macerated during an appropriate time, in the absence of light, agitated slowly and filtered in a manner as to obtain the first coloured extract. The operation is repeated with extraction by maceration with a hydro-alcoholic solvent (5% alcohol) following the same procedure as above, agitating slowly and filtering in a manner as to obtain a second coloured extract. Both extracts are concentrated together in a rotary evaporator at a temperature varying between 40 and 70° C., until attaining a final volume of 4.0 to 6.0% of the initial volume, thus, 1000 ml of initial extract will funish between 40 to 60 ml of concentrated extract.

Preferentially, the solution should be hydro-alcoholic and possess, apart from the colorant, an essence to give flavour to the composition. The alcoholic compound that should be added has the purpose of fixing the colorant to the plaque and may be selected from the group consisting of ethylic alcohol and other appropriate alcohol and may vary in concentration from between around 0 to 25% (v/v) of solution, and, more preferentially between 10 and 20% in the case of a composition based on the açai colorant and between 5 and 20% in the case of a composition based on the urucum colorant.

Preferentially, in the case of using colorants extracted from the fruit of the açai tree, the composition of the present invention presents the following ratios: 60 to 95% of concentrated solution extracted from acai, from 5 to 25% of a pharmaceutically acceptable vehicle and from 0 to 13% of pharmaceutically acceptable additives. Furthermore, in the case of colorants originating from urucum seeds, the solution comprises 58 to 90% of concentrated solution extracted from urucum seeds, from 9 to 25% of a pharmaceutically acceptable vehicle and from 0 to 13% of pharmaceutically acceptable additives. In the alternative of both the colorants extracted from açai fruit and the colorants extracted from urucum seeds being present, the composition, preferentially, comprises concentrated solutions of colorants extracted from açai and urucum in a proportion varying from 10:1 to 1:1.

Optionally, the solution may be aqueous and may contain around 30 to 40% by weight of glycerine or glycol propylene, gelatine, that function as dispersant and thickening agents, as well as imbuing a sweet flavour to the formulation.

Adequate flavorings may be employed in the alcoholic and aqueous composition and include, but are not limited to: (i) flavoring oils, such as mint, eucalyptus, peppermint, strawberry, grape, lemon, orange, sage, lime; (ii) synthetic flavoring, such as aldehydes, esters, alcohols and fatty compounds of high molecular weight known to those skilled in the art, such as menthol, amongst others.

Appropriate sweetening agents that may be added to the aqueous composition include saccharose, maltose, lactose, xylitol, sodium cyclamate, saccharine, amongst others.

The plaque evidencing compositions of the present invention may be prepared through the adequate mixture of the ingredients. For example, when preparing the aqueous solution the açai and/or urucum colorant is dissolved in water, to which may include the addition of, optionally, other hydrosoluble ingredients such as preservative, sweetening, flavorings, thickening and dispersant agents such as glycerine or a similar, providing they are pharmaceutically acceptable.

A comparative methodology is necessary to test the efficiency of the plaque evidencing colorants among the dental elements visualised as a quantitative of the plaque before and after applying the colorant to allow statistic treatment of the information.

The Simplified Visible Plaque Index is used to measure the initial bacterial plaque. To verify the efficiency of the colorant in evidencing plaque the same methodology of the above Index will be used adapted however, to a disclosing factor.

The Index of Visible Plaque (IVP) was described by Löe and Silness (LÖE, H; SILNESS, J. Periodontal Disease in Pregnancy. Acta Odontol. Scan. 21:533–51, 1963) and simplified by Axelsson and Lindhe (AXELSSON, P.; LINDHE, J. The effect of a preventive program on dental plaque, gingivites and caries in schoolchildren. Journal of Clinical Periodontology. 1:126–38, 1974). To obtain the IVP all the surfaces of teeth 16, 12, 24, 36, 32 and 44 are analysed in a manner that the plaque is confirmed without the aid of evidencing substances, considering therefore only the presence or absence of plaque visible to drying. In the case of any of the reference teeth being missing, they are not substituted.

Thus, IVP is determined by:

IVP=Number of teeth with plaque/Number of teeth examined×100

The measurement of the efficiency of the natural colorants is based on the Visible Plaque Index adapted to the use of colorants due to the fact that the same teeth must be analysed. In this manner the natural colorant from açai or urucum is applied to all the surfaces of teeth 16, 12, 24, 36, 32 and 44. In the case of any of the reference teeth being missing, they are not substituted.

Thus, IVP is determined by:

IVP=Number of teeth stained/Number of teeth examined×100

The following examples are illustrative of the invention and represent preferential embodiments. Those skilled in the art will know of or will be able to employ not more than routine experimentation to encounter other materials or techniques, such as alcoholic solutions, flavorings, amongst others.

EXAMPLE 1

Extraction of the Açai (*Euterpe oleracea*) Colorant

One part of ripe açai fruit is added to one and a half parts of a hydro-alcoholic solution at 20% of ethylic alcohol. The product is left to cold macerate during 48 hours in a dark place, during which the product is slowly agitated 4 times a day following which it is filtered in a manner as to obtain a first coloured extract which is then kept under refrigeration. The operation of extraction by maceration is repeated with a new solution of ethylic alcohol at the same concentration as before, for another 48 hours, following the same procedure and being slowly agitated 4 times a day. The solution is filtered thus obtaining the second coloured extract. Both extracts are combined and concentrated in a rotary evaporator until attaining approximately 10% of its initial volume (1000 ml) at a temperature between 50 and 60° C.

EXAMPLE 2

Extraction of the Urucum (*Bixa orellana*) Colorant

One part of urucum seeds are added to two parts of a hydro-alcoholic solution at 5% of ethylic alcohol. The product is left to cold macerate during 48 hours in a dark place, during which the product is slowly stirred 4 times a day following which it is filtered in a manner as to obtain a first coloured extract which is then kept under refrigeration. The operation of extraction by maceration is repeated with a new solution of ethylic alcohol at the same concentration as before, for another 48 hours, following the same procedure and being slowly stirred 4 times a day. The solution is filtered thus obtaining the second coloured extract. Both extracts are combined and concentrated in a rotary evaporator until attaining approximately 8% of its initial volume (1000 ml) at a temperature between 50 and 60° C.

EXAMPLE 3

Aqueous Formulation of the Composition Based on the Açai Colorant 7 ml of anthocyanins colorants extracted in accordance with Example 1 are added to 30 ml of distilled water; 2.5 ml of bidistilled glycerine; 1.3 grams of sodium saccharine and 0.1 ml of edible strawberry essence. The concentration (v/v) of the different components in the final product are as follows:

| | |
|---|---|
| Concentrated solution of açai colorants | 17.1% |
| Edible strawberry essence | 0.3% |
| Distilled water | 73.3% |
| Bidistilled glycerine | 6.1% |
| Sodium saccharine | 3.2% |

The final product presented a sweet taste with slight bitterness.

EXAMPLE 4

Alcoholic Formulation of the Composition Based on the Açai Colorant 9 ml of anthocyanin colorant extracted in accordance with Example 1 are added to 3 ml of ethylic alcohol and 0.05 ml of edible strawberry essence. The concentration (v/v) of the different components in the final product are as follows:

| | |
|---|---|
| Concentrated solution of açai colorants | 74.7% |
| Ethylic alcohol at 92.8° GL | 24.9% |
| Edible strawberry essence | 0.4% |

This concentration of flavoring proved insufficient and did not impart definite flavour to the final product.

EXAMPLE 5

Alcoholic Formulation of the Composition Based on the Açai Colorant 6 ml of anthocyanin colorant extracted in accordance with Example 1 are added to 0.3 ml of ethylic alcohol and 0.25 ml of edible strawberry essence. The concentration (v/v) of the different components in the final product are as follows:

| | |
|---|---|
| Concentrated solution of açai colorants | 91.6% |
| Ethylic alcohol at 92.8° GL | 4.6% |
| Edible strawberry essence | 3.8% |

EXAMPLE 6

Alcoholic Formulation of the Composition Based on the Açai Colorant 6 ml of anthocyanin colorant extracted in accordance with Example 1 are added to 0.7 ml of ethylic alcohol and 0.25 ml of edible strawberry essence. The concentration (v/v) of the different components in the final product are as follows:

| | |
|---|---|
| Concentrated solution of açai colorants | 86.3% |
| Ethylic alcohol at 92.8° GL | 10.1% |
| Edible strawberry essence | 3.6% |

This formulation presented the most defined flavour and the best bonding to plaque.

EXAMPLE 7

Aqueous Formulation of the Composition Based on the Urucum Colorant 5 ml of urucum extract (bixin and norbixin colorant) extracted in accordance with Example 2 are added to 30 ml of distilled water; 2.5 ml of bidistilled glycerine; 1.5 grams of sodium saccharine and 0.1 ml of edible strawberry essence. The concentration (v/v) of the different components in the final product are as follows:

| | |
|---|---|
| Concentrated solution of urucum colorants | 12.8% |
| Distilled water | 76.7% |
| Glycerine | 6.4% |
| Sodium saccharine | 3.8% |
| Edible strawberry essence | 2.5% |

EXAMPLE 8

Alcoholic Formulation of the Composition Based on the Urucum Colorant 9 ml of colorant (bixin and norbixin) extracted in accordance with Example 2 are added to 3 ml of ethylic alcohol and 0.1 ml of edible strawberry essence. The concentration (v/v) of the different components in the final product are as follows:

| | |
|---|---|
| Concentrated solution of urucum colorants | 74.4% |
| Ethylic alcohol at 92.8° GL | 24.8% |
| Edible strawberry essence | 0.8% |

The final product presented a peppery flavour but a good bonding to plaque.

EXAMPLE 9

Alcoholic Formulation of the Composition Based on the Urucum Colorant 25 ml of colorant (bixin and norbixin) extracted in accordance with Example 2 are added to 3 ml of ethylic alcohol and 0.25 ml of edible strawberry essence. The concentration (v/v) of the different components in the final product are as follows:

| | |
|---|---|
| Concentrated solution of urucum colorants | 88.5% |
| Ethylic alcohol at 92.8° GL | 10.6% |
| Edible strawberry essence | 0.9% |

The final product presented a well defined flavour.

EXAMPLE 10

Alcoholic Formulation of the Composition Based on the Urucum Colorant 25 ml of colorant (bixin and norbixin) extracted in accordance with Example 2 are added to 4.5 ml of ethylic alcohol and 0.35 ml of edible strawberry essence. The concentration (v/v) of the different components in the final product are as follows:

| | |
|---|---|
| Concentrated solution of urucum colorants | 83.7% |
| Ethylic alcohol at 92.8° GL | 15.1% |
| Edible strawberry essence | 1.2% |

The final product presented a well defined flavour.

EXAMPLE 11

Alcoholic Formulation of the Composition Based on the Urucum Colorant 25 ml of colorant (bixin and norbixin) extracted in accordance with Example 2 are added to 6.25 ml of ethylic alcohol and 0.35 ml of edible strawberry essence. The concentration (v/v) of the different components in the final product are as follows:

| | |
|---|---|
| Concentrated solution of urucum colorants | 79.1% |
| Ethylic alcohol at 92.8° GL | 19.8% |
| Edible strawberry essence | 1.1% |

This was the formulation that presented the best bonding to plaque and had a well defined flavour.

EXAMPLE 12

Evaluation of the Efficiency of Evidencing with Natural Colorants.

The efficiency tests using bacterial plaque evidencing with colorant from the açai (dark red colour) and with colorant from urucum (orange colour) were undertaken on 48 randomly chosen persons. The results shall be analysed considering a reliability margin of 95% and a sample error of 5%.

The evaluation of the efficiency of the different colorants was performed on the same person at a minimum interval of 48 hours between one analysis and another and that person could not do any oral hygiene for a minimum period of 6 hours before the test, but fasting was not required in this period.

In the first analysis, employing the Visible Plaque Index the presence or absence of plaque was observed on teeth 16, 12, 24, 36, 32 and 44. Afterwards, with the aid of a paintbrush, all the surfaces of the reference teeth were given a coating of the evidencing solution of natural colorant (firstly the evidencing solution of açai colorant and 48 hours later the urucum colorant) after which an analysis was done through the Visible Plaque Index adapted for the use of natural colorant. In this manner it was possible to evaluate the efficiency of the evidencing solution.

To obtain the results the Visible Plaque Index was compared to the Index for plaque with the natural colorant. The T test was employed to compare the plaque evidencing with açai and urucum colorants and the visible plaque, with a significance level of $p=0.01$.

Table 1 shows the efficiency of the açai colorant by the comparison of the VPI with the index of plaque with colorant.

TABLE 1

Verification of the açai colorant efficiency through comparison between the VPI and the index of plaque with colorant.

| | No. of teeth with plaque without use of colorant | No. of teeth with plaque with acai colorant |
|---|---|---|
| Average | 3.083 | 5 |
| Variance | 3.270 | 1.234 |
| Observations | 48 | 48 |
| Pearson's correlation | 0.519 | |
| Hypothesis of average distance | 0 | |
| Gl | 47 | |
| Stat t | −8.539 | |
| Uni-caudal P (T ≦ t) | 2.023E − 11 | |
| Uni-caudal critical T | 1.678 | |
| Bi-caudal P (T ≦ t) | 4.046E − 11 | |
| Bi-caudal critical T | 2.012 | |

Figure 1:
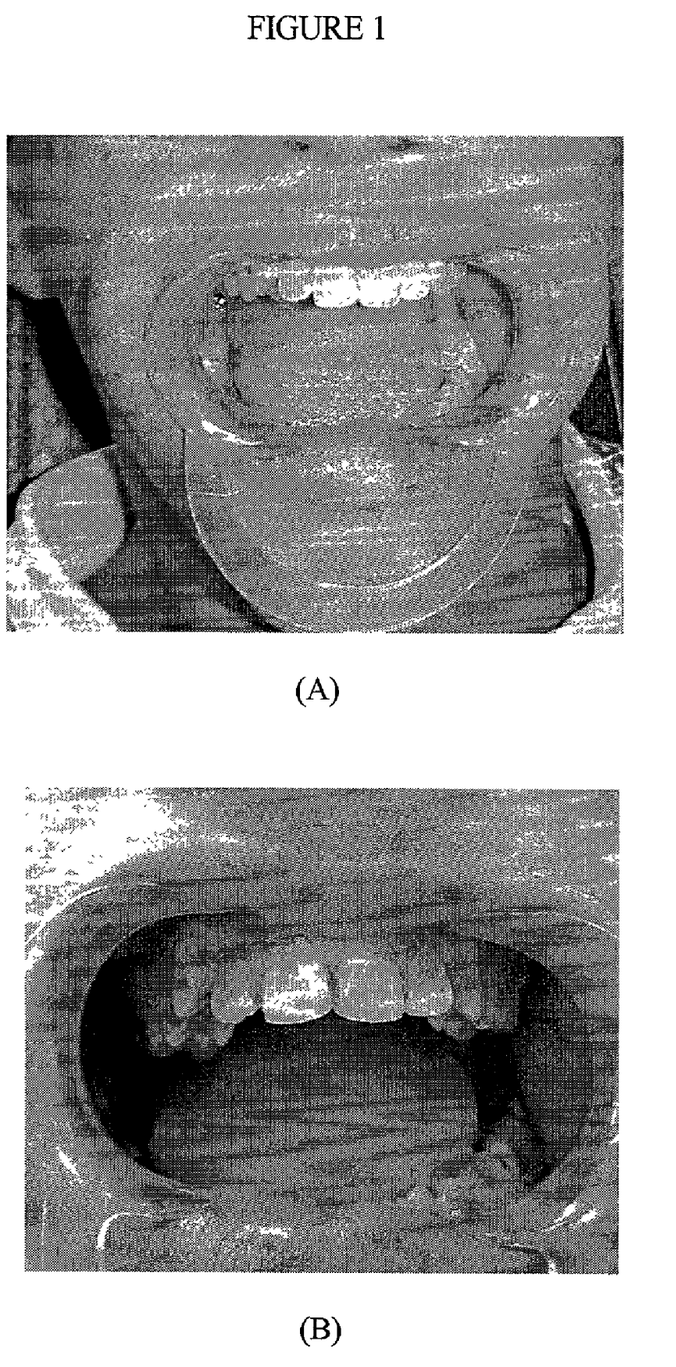
FIG. 1: Shows in (a) the visualisation of the plaque before using the evidencing agent and in (b) the visualisation of the plaque after evidencing with açai (*Euterpe oleracea*) colorant (anthocyanins).
Figure 2:
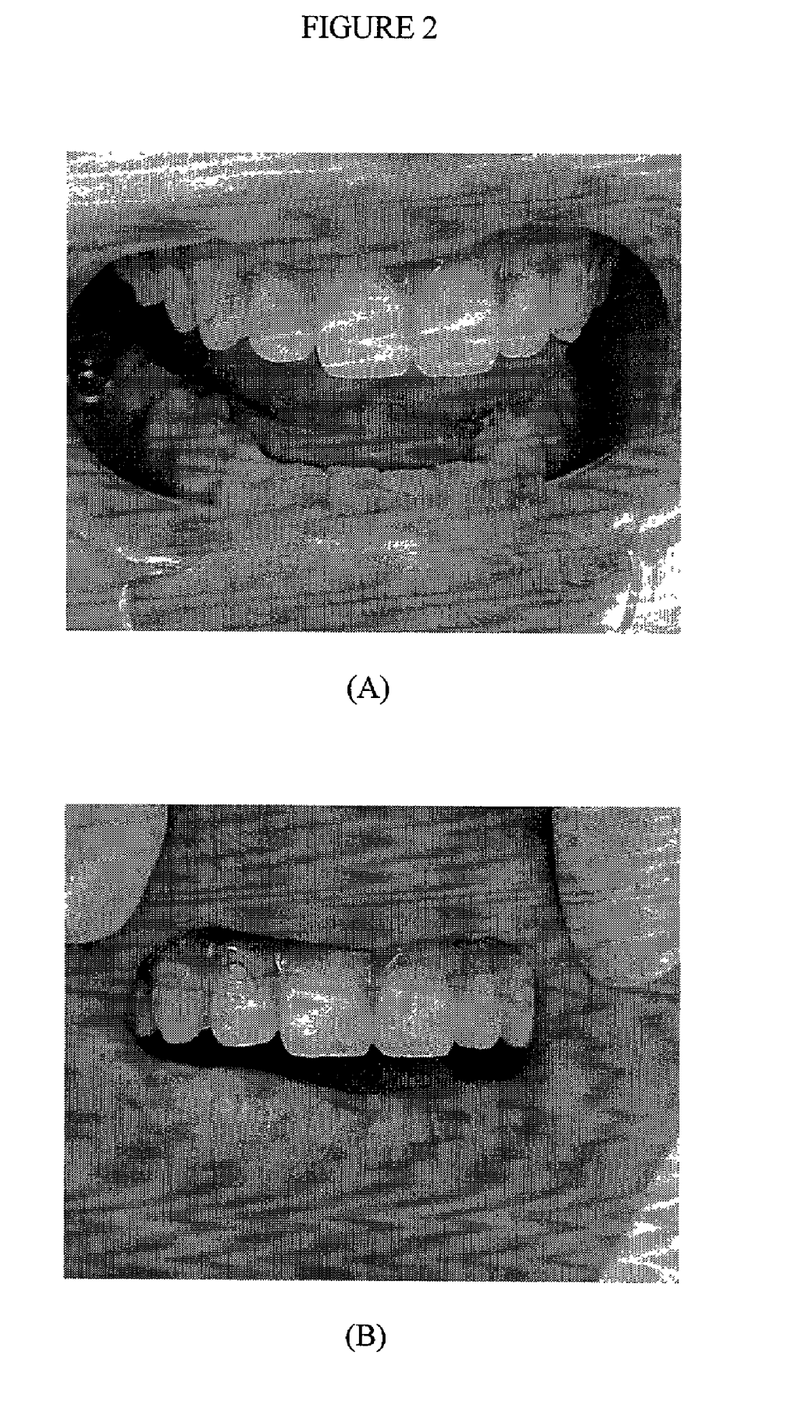
FIG. 2: Illustrates in (a) the visualisation of the plaque before using the evidencing agent and in (b) the visualisation of the plaque after evidencing with urucum (*Bixa orellana*) colorant (bixin and norbixin).

When the visible plaque and the açai colorant are compared it can be seen that the colorant identified more teeth with plaque than the observation of plaque without colorant. FIG. 1 presents these results.

TABLE 2

Verification of the urucum colorant efficiency through comparison between the VPI and the index of plaque with colorant.

| | No. of teeth with plaque without use of colorant | No. of teeth with plaque with urucum colorant |
|---|---|---|
| Average | 3.167 | 2.229 |
| Variance | 1.503 | 2.478 |
| Observations | 48 | 48 |
| Pearson's correlation | 0.542 | |
| Hypothesis of average distance | 0 | |
| Gl | 47 | |
| Stat t | 4.725 | |
| Uni-caudal P (T ≦ t) | 1.059E−05 | |
| Uni-caudal critical T | 1.678 | |
| Bi-caudal P (T ≦ t) | 2.117E−05 | |
| Bi-caudal critical T | 2.0117 | |

Figure 3:
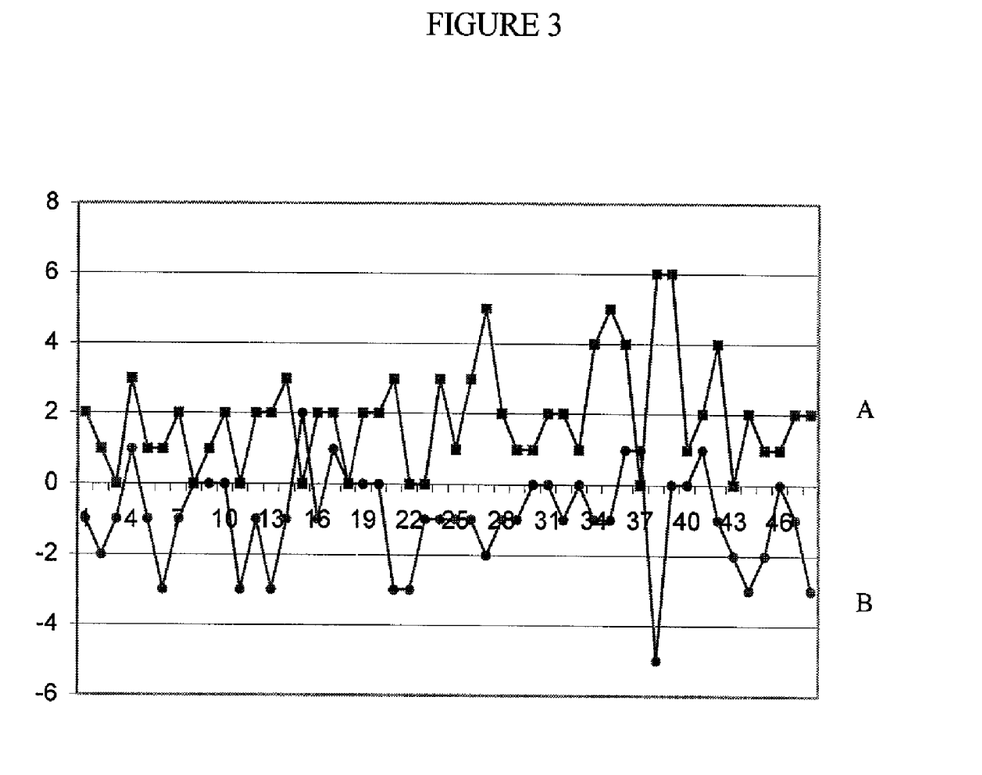
FIG. 3: Shows the comparison between the efficiency of the açai (*Euterpe oleracea*) (A) and urucum (*Bixa orellana*) (B) colorants.

Finally, Table 3 shows the compared efficiency of both colorants. When calculating the margin of precision of both methods it can be noted that the urucum colorant does not colour an average of 0.93 teeth with plaque whilst the açai colorant coloured an average of 1.93 more than the visual method. FIG. 3 presents these results graphically (A=açai colorant and B=urucum colorant).

TABLE 3

Comparison and efficiency of the açai and urucum colorants.

| | Dif-Urucum | Dif-Acai |
|---|---|---|
| Average | −0.938 | 1.917 |
| Variance | 1.890 | 2.42 |
| Observations | 48 | 48 |
| Pearson's correlation | −0.157 | |
| Hypothesis of average distance | 0 | |
| Gl | 47 | |
| Stat t | −8.862 | |
| Uni-caudal P (T ≦ t) | 6.788E−12 | |
| Uni-caudal critical T | 1.678 | |
| Bi-caudal P (T ≦ t) | 1.357E−11 | |
| Bi-caudal critical T | 2.012 | |

Despite not showing the same efficiency as the açai colorant, the urucum colorant has the potential to be used for plaque evidencing and because it is a product of natural origin is certainly of interest to the pharmaceutical industry and could be recommended for persons sensitive to anthocyanins, for example.

What is claimed is:

1. A bacterial plaque evidencing composition comprising:
   (i) at least one concentrated solution of natural colorants, said concentrated solution of natural colorants being obtained from açai (*Euterpe oleracea*) by an extraction process comprising adding alcohol-containing agueous solution to ripe açai fruit, cold maceration in the absence of light, and concentration of the resulting extract; and
   (ii) a pharmaceutically acceptable vehicle, wherein the composition is effective to color bacterial plaque formations.

2. The composition according to claim 1 further comprising pharmaceutically acceptable additives.

3. The composition according to claim 1 wherein the pharmaceutically acceptable vehicle is selected from the group consisting of water, alcohol or their mixtures.

4. The composition according to claim 2 having at least one pharmaceutically acceptable additive selected from the group consisting of thickeners, flavorings, sweeteners, dispersants and preservatives.

5. The composition according to claim 4 wherein the thickener is selected from the group consisting of glycerine, glycol propylene, gelatine and their mixtures.

6. The composition according to claim 4 wherein the flavoring is selected from the group consisting of natural flavoring oils, synthetic flavorings and their mixtures.

7. The composition according to claim 2 comprising from 60 to 95% of the at least one concentrated solution of natural colorants, from 5 to 25% of pharmaceutically acceptable vehicles, and from 0 to 13% of pharmaceutically acceptable additives.

8. A method of disclosing oral bacterial plaque comprising contacting teeth with the evidencing composition according to claim 1.

9. A process of using the evidencing composition of claim 1 comprising:
   (i) conventional cleaning of the oral cavity;
   (ii) direct application of said composition to the surface of the teeth; and (iii) mechanical removal of the bacterial plaques evidenced by the said evidencing composition.

\* \* \* \* \*